(12) United States Patent
Palestro et al.

(10) Patent No.: US 6,497,840 B1
(45) Date of Patent: Dec. 24, 2002

(54) ULTRAVIOLET GERMICIDAL SYSTEM

(76) Inventors: Richard P. Palestro, 121 72 E. 2nd Dr., Aurora, CO (US) 80011; Dale R. Morgan, 3173 Racine St., Aurora, CO (US) 80010; Michael Dee Iseman, 4949 S. El Camino Dr., Englewood, CO (US) 80111; Donald P. Rosier, 13761 W. 59th Ave., Arvada, CO (US) 80004

( * ) Notice: Subject to any disclaimer, the term of this patent is extended or adjusted under 35 U.S.C. 154(b) by 0 days.

(21) Appl. No.: 08/147,776

(22) Filed: Nov. 8, 1993

Related U.S. Application Data

(63) Continuation-in-part of application No. 08/087,178, filed on Jul. 2, 1993, now abandoned, which is a continuation-in-part of application No. 07/960,085, filed on Oct. 9, 1992, now abandoned.

(51) Int. Cl.⁷ ................................................. A61L 2/10
(52) U.S. Cl. ................. 422/24; 422/4; 422/5; 422/117; 422/121; 422/186.3; 250/432 R; 250/436; 250/437; 250/438; 96/223; 96/224
(58) Field of Search ............................ 422/24, 292, 4, 422/5, 117, 121, 186.3; 250/432 R, 435, 436, 437, 438; 96/223, 224

(56) References Cited

U.S. PATENT DOCUMENTS 3,072,978 A * 1/1963 Minto
3,757,495 A * 9/1973 Sievers

* cited by examiner

Primary Examiner—Marian C. Knode
Assistant Examiner—Basia Ridley
(74) Attorney, Agent, or Firm—Gibson, Dunn & Crutcher LLP

(57) ABSTRACT

A germicidal method and apparatus for destroying airborne pathogenic bacteria such as tuberculosis bacteria using ultraviolet light. Air is drawn through a filter and into a sterilization chamber that is irradiated with ultraviolet light, and out through an exhaust opening. Consideration for the characteristics of the room in which the apparatus is installed and the positioning of the installation allows effective prevention of transmission of disease through expectoration and inhalation of airborne microdroplets of bacteria-containing sputum. The filter is of the low-density type which traps large particulates, but not small particulates of the size of the microdroplets, so that the filter does not become a bacteria colonization site. Baffles on the air intake opening and air exhaust opening to prevent ultraviolet light from escaping into the environment.

8 Claims, 2 Drawing Sheets

ULTRAVIOLET GERMICIDAL SYSTEM

This application is a continuation-in-part of application Ser. No. 08/087,178 filed Jul. 2, 1993, now abandoned, which is a continuation-in-part of application Ser. No. 07/960,085 filed Oct. 9, 1992 now abandoned.

FIELD OF THE INVENTION

The present invention relates to the field of germicidal systems employing bacteria-destroying ultraviolet lights. In particular, the present invention relates to a system for producing an air flow through a baffled ultraviolet sterilization chamber, wherein the ultraviolet light intensity, the air residency time, and the air exchange rate for the air volume in a given space, are such that a percentage of tuberculosis bacteria are destroyed that effectively prevents transmission of such disease by airborne sputum.

BACKGROUND OF THE INVENTION

Tuberculosis is the most common cause of death from infectious disease in the world today. It infects millions of people each year and causes hundreds of thousands of fatalities. The disease is particularly prevalent in less-industrialized countries where high population densities, poor sanitary conditions and a high percentage of individuals in poor health contribute to the spread of infectious diseases.

After a long period of declining rates of tuberculosis infection in the United Sates, it is believed that the infection rate is now increasing. The increasing rate is apparently due to a combination of factors. One factor is undoubtedly increased immigration from parts of the world with high rates of infection. For example, in the United States the case rate of tuberculosis per 100,000 population was 9.3 in 1985, resulting in over 22,000 cases and over 1,200 deaths. In Southeast Asia, both the case rate and the death rate are believed to be many times that, and immigrants from that part of the world now constitute 3 to 5% of new cases in the United States.

Another factor related to increased rates of tuberculosis infection appears to be the use of living quarters with high population densities and less-than-ideal sanitary conditions for persons in ill health who are susceptible to the disease. Such conditions are commonly found in shelters for the homeless, prisons and some nursing homes. Another important factor in the increased rate of infection is infections among patients with Acquired Immune Deficiency Syndrome (AIDS) and intravenous drug users.

Another reason for the recent increased incidence of tuberculosis is probably the failure of many medical professionals to diagnose and treat the disease early and properly. The relative rareness of the disease in the United States since the early epidemics resulted in an entire generation of health care workers without much experience in the disease. Further, diagnosing the disease is not always easy, for the symptoms are similar to the symptoms of many other disorders. Therefore, the disease is often misdiagnosed and mistreated, and the degree of infectiousness of the disease is underappreciated.

Even after it is recognized that a set of symptoms may indicate tuberculosis, the tests for the disease are somewhat imprecise and tend to require judgment by an experienced professional. For example, one diagnostic tool is chest x-rays which typically show apical-posterior segment cavitary changes in tuberculosis infected patients. However, in elderly individuals—who comprise a relatively large proportion of tuberculosis patients—lobar or patchy lower-zone shadows may simulate bacterial or aspiration pneumonia. Also, x-rays in the elderly may mislead the physician by showing a solitary pulmonary nodule or a pleural effusion. Another important tuberculosis test is the tuberculosis skin test, but a major disadvantage to the tuberculosis skin test is that it generates a high number of both false-positive and false-negative results. The most precise test is microscopic examination of a sputum sample, but this test may require the use of at least three separate samples of sufficient volume, which may require gastric aspiration or bronchoscopy in patients with low sputum production.

The normal body reaction to infection by tuberculosis bacteria is to build a fibrous wall around each bacterium. Initially, a person may be unaware of any infection, but over a period of months or even years the infection produces inflammation and eventually destruction of tissue. The manifestations as the disease progresses generally include cough, fever, night sweats, hemoptysis, chest pain, weight loss and malaise. The usual treatment for tuberculosis is administration of drugs over a period of many months such as isoniazid, rifampin and pyrazinamide and ethambutol. Persons recently infected but with no active disease are usually given isoniazid preventive therapy, particularly if they have other risks such as malnutrition, gastrectomy, diabetes mellitus, pneumoconiosis, malignancy or if for some reason they have immunosuppression such as from corticosteroid therapy, renal impairment or HIV infection. In short, tuberculosis in a normal healthy patient is typically a disease that is curable by drugs, although the drug therapy is quite prolonged.

A serious concern—and yet another reason for the recent increase in tuberculosis—is the development of drug-resistant tuberculosis. It is estimated that at least 5% of new cases are resistant to the usual drug therapy, and that the percentage in some areas of the United States is as high as 20%. While non-drug-resistant tuberculosis is typically 99% curable in patients with normal immune responses, drug-resistant tuberculosis is only about 50–60% curable. A related concern is drug therapy on non-drug-resistant tuberculosis for patients who are intolerant of the drugs. In those cases, drug therapy is complicated because the drug is effective against the infection but has serious adverse effects on the patient such as hepatitis or serious rashes.

Another concern is raised by the increasing incidence of non-tuberculosis mycobacterial pulmonary infections. Many such infections produce symptoms similar to those of tuberculosis infections, but may be more difficult to identify and treat. Moreover, they may be transmitted through the same means as tuberculosis and tend to infect the same types of susceptible individuals.

The transmission of the tuberculosis bacteria is accomplished almost exclusively by infected individuals expectorating microdroplets of bacteria-containing sputum by coughing or sneezing. These microdroplets are suspended in the air and are inhaled by other individuals in the vicinity. The bacteria typically lodges in the lower lung where it proliferates, and may be disseminated to other organs as well. The microdroplets of sputum which contain the bacteria may be very small—on the order of 0.01 microns. In fact, it appears that the smallest droplets are the most effective in communicating the disease since the smallest droplets stay airborne indefinitely and are easily inhaled to the lower lung where they are not readily removed. Studies have shown that aerosol droplets on the order of 1–5 microns are highly effective vehicles for transmitting the disease.

One controversial approach to combatting the disease has been the use of vaccines. However, the efficacy of tuberculosis vaccines is debatable. Even the trials which seemed to show some efficacy have shown less efficacy among adults than among infants and children. An additional objection to widespread vaccinations is that by inducing tuberculin reactivity in the population they would confound the detection and measurement of infections through the use of skin tests, since skin tests in vaccinated individuals would presumably result in a false-positives. This would severely curtail the practice of preventive drug therapy among infected patients who have not yet developed outward symptoms.

The airborne aspect of the disease has led toward systems for preventing the transmission of the disease which focus on filtration and sterilizing devices. One approach is the use of masks. Simple surgical masks are thought to be insufficient in view of the very small size of the sputum microdroplets which are effective in communicating the bacteria. Instead, disposable particulate respirators are recommended. The use of masks is fraught with practical difficulties; they are physically uncomfortable, they impair breathing (which is already impaired for many patients), and they disrupt speaking. To be effective at all, it would probably be necessary for the masks to be worn not just by the patients, but also by noninfected individuals. In view of the long distances that airborne microdroplets containing viable bacteria can travel, it would be necessary for the masks to be worn by noninfected individuals throughout the general vicinity of a patient and not just those in the immediate presence of a patient. Moreover, it is not known for certain whether the use of masks would actually be effective even if the practical problems were tolerated or overcome.

Another preventive measure which relies on the airborne aspect of the bacteria is the use of modified ventilation systems. It is currently recommended that facilities used for tuberculosis patients undergo certain minimum air exchange rates, under the theory that dilution of infectious air with clean air will reduce the concentration of bacteria and hence the likelihood of transmission of the disease. While this approach is theoretically sound, it is problematic in implementation. Modern buildings are normally designed with fixed ventilation systems which are not easily modified to produce the requisite air exchange rate. Even if they are suitably modified, they may be rendered ineffective by an open door or by shifting air-flow patterns. A high air exchange rate also increases cooling and heating costs. Finally, there is the issue of the ultimate disposition of the contaminated air that is removed, and whether it is appropriate to simply release it outside the facility.

Another approach to reducing the transmission of the disease is the use of high-efficiency filtration systems. For such a system to be effective, however, it must employ a very dense filter to trap very small particles. This entails a powerful fan, high energy usage, loud noise, and meticulous installation and maintenance. There is also concern that the filters and the rest of the air-flow path may themselves become sites of bacteria colonization.

Yet another approach to reducing the transmission of the tuberculosis bacterial employs ultraviolet light as a germicide. It was discovered some time ago that airborne bacteria are susceptible to ultraviolet light in wavelengths of about 254 nm. Wells S. F., *On Air-Borne Infection: II-Droplets and Droplet Nuclei*, Am. J. Hyg. 1934 20: 611–8; Wells W. F., Fair G. M., *Viability of E. Coli Exposed to Ultraviolet Radiation in Air*, Science 1935; 82:280–1. That finding led to the development of systems using ultraviolet light as a germicide against airborne bacteria such as measles and tuberculosis. However, interest in such systems diminished when later investigators were unable to obtain the desired efficacy. Also contributing to the diminished interest in such systems was the recognition that ultraviolet lights produced harmful ozone and also produced skin and eye irritation. With the development of streptomycin and chemotherapy for tuberculosis treatment, the belief became prevalent that tuberculosis would be eradicated and that preventive systems would be unnecessary.

The systems that were developed using ultraviolet light as a germicide against tuberculosis were imprecise, marginally effective, and perhaps dangerous. The most common system simply employed ultraviolet lights mounted on or suspended from a wall or ceiling of a room. For example, a system employing lights suspended from the ceiling is described in some detail in Riley, R. Z., Knight, M. and Middlebrook, G., *Ultraviolet Susceptibility of BCG and Virulor Tubercle Bacilli*, Am. Rev. of Resp. Dis., 1976, 113:413. The problems in such a system are numerous. It relies completely on normal air circulation in the room where it is installed to bring the bacteria within range of the ultraviolet light. The normal circulation in a room may be too low for the ultraviolet light to destroy a necessary proportion of bacteria, or the normal circulation may be high enough but of a pattern that does not bring the airflow past the ultraviolet light. Moreover, there is no single test to determine whether the circulation rate and patterns are adequate or not for a given installation. Further, such systems quickly become contaminated by dust on the light bulbs which diminishes their effectiveness. From a safety standpoint, one of the greatest concerns is that the simple light shields used with such systems allow light to be reflected off the walls and ceiling and onto the skin and eyes of the occupants. The degree of danger associated with the indirect ultraviolet irradiation is disputed, but there is undoubtedly at least some danger if the period of exposure is prolonged. In explaining the necessary safety precautions, Riley, R. L. and Nordell, E.A., *Clearing the Air, The Theory and Application of Ultraviolet Air Disinfection*, Am. Rev. Respir. Dis. 1989 139:1286, stated:

> Does germicide UV cause inflammation of skin and eyes? It can, but the standard set by the National Institute of Occupational Safety and Health (NIOSH) is very conservative. Overhead installations must be inspected for 'hot spots' (greater than 0.2 uW/cm$^2$) with a sensitive UV meter. Installers should anticipate readjusting fixture height up or down based on meter readings. Baffles designed to prevent direct eye contact will also need adjustment after the initial installation. Excessively reflective surfaces about fixtures may contribute to excess radiation, but this can be reduced with nonreflective paint or by spraying the surface with stove black. If the intensity of UV does not exceed 0.2 uW/cm$^2$, the likelihood of skin or eye irritation is minimal during an 8-$h$ exposure. Persons with especially sensitive skin, with systemic lupus erythematous, for example, may need to avoid exposure or take measures to protect their skin.

This illustrates some of the difficulties and dangers of employing ultraviolet lights behind a simple light shield; the light may generate dangerous and unpredictable "hot spots", it is not appropriate for those with sensitive skin or eyes, and it requires careful consideration of the placement and the orientation and reflectivity of the surrounding surfaces. Finally, even if all those precautions are observed, the quote only indicates that skin and eye irritation is "minimal" rather than nonexistent and only for exposure periods of 8 hours. Of course, for the system to be effective against transmission of airborne disease in, for example, a patient room, it would have to operate continuously and not just for 8 hour periods. The article goes on to acknowledge that:

> UV or disinfection that is inappropriately applied, poorly planned, or carelessly used may be ineffective, dangerous, and falsely reassuring. The guidelines and precautions listed above are not intended to enable a would-be user of UV to plan, purchase, install, or check the adequacy of a UV installation. Detailed instructions for UV installers have been published. However, there is currently little commercial interest in UV for air disinfection and, therefore, little expert guidance for comprehensive planning and installation. Renewed consumer interest may stimulate the UV industry to correct this deficiency.

Notwithstanding the uncertainly expressed in the Riley and Nordell article regarding the dangers of ultraviolet radiation, that article is actually more cognizant of those dangers than much of the other literature on the subject. For example, the article by Riley, Knight and Middlebrook, *supra*, does not even mention the dangers to the skin and eyes of ultraviolet radiation, or any precautions that should be taken to minimize those dangers.

There are number of ultraviolet germicidal systems that have been patented, but as in the case of the scientific literature mentioned above, those patents teach little about the dangers of ultraviolet radiation and how to effectively minimize the dangers, or how to position and operate the devices to achieve the requisite bacterial kill rate to prevent transmission of disease.

For example, U.S. Pat. No. 3,975,790 by Patterson is for an ultraviolet lamp fixture used in combination with a conventional commercial vacuum cleaner, and U.S. Pat. No. 4,087,925 by Bienek is for a sterilizing hand dryer, in which ultraviolet lights are positioned within the housing of a blower that is used to dry wet hands, where the blower is of the type commonly used in commercial restrooms. The devices of Patterson and Bienek seem to include little or nothing for light baffling to prevent leakage of allowable light to outside the housing, and the patents teach nothing about optimal flow rates, air-exchange rates or other information for the effective use of the machines. The devices are obviously intended as general, and only partially effective, sterilizing tools rather than as comprehensive and predictably effective systems.

Another patent, U.S. Pat. No. 4,210,429 by Golstein, employs a "squirrel-cage" type blower which draws air into a housing through a air intake filter, through the blower, and through a sterilization chamber containing ultraviolet lights. The air leaves the sterilization chamber, passes through a second filter and a charcoal filter and finally exits through an outlet. The specification indicates that the purpose of the device is to remove "pollens, lung damaging dust, smoke, bacteria and any one of a number of other irritants and micro-organisms" and that it does so for "particles down to 0.3 microns in size with an efficiency of 99.9%". The device is characterized as an "air purifier" rather than as a germicidal device; the use of three distinct filters including a very fine filter for removing extremely small particles, a charcoal filter for removing odors and a pre-filter for removing particles, is distinguishable in design and function from the present invention. This extensive filtration would require a high-capacity blower to achieve any effective air exchange rate. The device is not specifically designed for destroying the tuberculosis bacteria or any other specific bacteria, although it would obviously be effective in doing so to some extent. Therefore, the patent teaches nothing about the use of the device for that purpose or the optimal flow rates or positioning of the device for that purpose.

U.S. Pat. No. 5,074,894 by Nelson is for a hospital room to quarantine patients with tuberculosis or other respiratory diseases caused by airborne pathogens. Although one embodiment of the system includes an air circulation circuit with ultraviolet lights, the patent is directed primarily toward negative pressure and filtering aspects utilizing high-efficiency particulate air filters.

Other patents describing the use of ultraviolet light as a germicide against airborne bacteria include, U.S. Pat. Nos. 4,448,750 by Fuesting, 4,896,042 by Humphreys, 4,990,311 by Hirai and 4,047,072 by Wertz. Patents directed toward the use of ultraviolet light as a germicide against bacteria in water or other liquids include U.S. Pat. Nos. 4,400,270 by Hillman, 4,482,809 by Maarschalkerweerk, 5,102,450 by Stanley and 5,124,131 by Wekhof.

SUMMARY OF THE INVENTION

The present invention is an apparatus and process for destroying airborne pathogenic bacteria such as the tuberculosis bacteria. Ultraviolet lights of a sufficient intensity are positioned within a sterilization chamber where they irradiate an air stream containing the bacteria, typically in the form of suspended microdroplets of sputum. The sterilization chamber has an exit and an entrance, and a blower is positioned preferably at the exit to draw air into the entrance and through the sterilization chamber and out the exit. The air passing through the sterilization chamber is virtually completely sterilized of viable tuberculosis bacteria by the chosen dosimetry of the system, which is achieved by appropriately sizing the sterilization chamber employing ultraviolet lights of the correct intensity, and utilizing the right air flow rate through the blower.

The sterilization chamber includes a filter on the intake side to filter out large particles such as dust, in order to minimize the contamination of the ultraviolet light bulbs. The filter is deliberately designed not to intercept small particles such as microdroplets, since the filter could then become a bacteria colony. The use of a low density filter also minimizes the resistance to air flow, thereby allowing the use of a smaller, more efficient and quieter blower. With the exception of this intake filter for removing large particulates, the apparatus preferably does not include any devices that would intercept and retain microdroplets or other small particles in a way that resists the air flow and poses the possibility of becoming a bacteria colonization site; the small particulates and microdroplets with destroyed bacteria simply pass through the apparatus and are expelled back into the environment.

Both the air intake and exhaust to the sterilization chamber are baffled so that ultraviolet light must reflect off multiple surfaces before exiting the sterilization chamber. The interior surfaces of the baffles may be light-absorptive to minimize their reflectivity and further lessen the possibility of ultraviolet light leaking from the sterilization chamber into the environment.

The apparatus is used in a space having a volume of air that results in an air exchange rate of preferably 12–15 air exchanges per hour. At that air exchange rate, it has been determined that a sufficient volume of air will circulate through the apparatus and will prevent any air stagnation in the room, that a high enough percentage of tuberculosis bacteria will be destroyed before they are inhaled by persons in the room to prevent transmission of the disease. The apparatus is preferably positioned such that the air intake is approximately at the head level of a seated patient, so that the air intake draws the air volume containing the highest level of bacteria-containing sputum microdroplets expectorated from the patient's pulmonary system.

DESCRIPTION OF THE PREFERRED EMBODIMENTS

Figure 1:
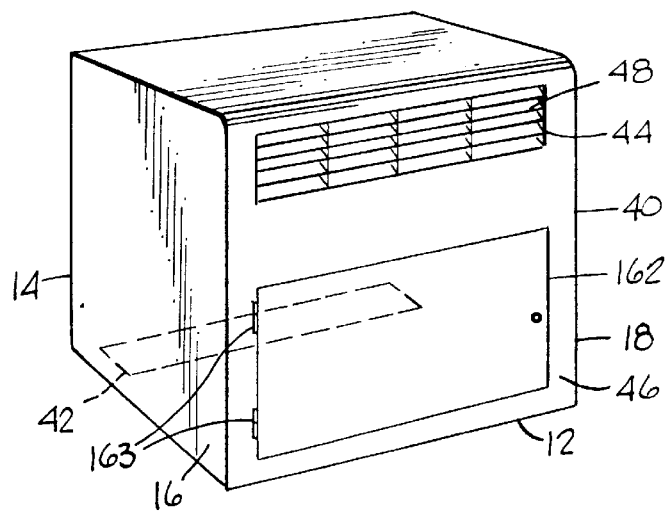
FIG. 1 is a pictorial view of the present invention.

A pictorial view of a preferred embodiment of the invention is shown in FIG. 1. The principal elements of the invention 10 include an exterior housing 40 having an air intake 42 and an air discharge 44, a motor 110 and associated blowers 120 and 130, an ultraviolet light box 150 within the housing 40. The air intake 42 is preferably positioned on the bottom 12 of the housing toward the rear wall 14 of the unit and extends from one sidewall 16 to the opposite sidewall 18. As better shown in the sectional view of FIG. 2, the air intake 42 has positioned within it a filter 60 which substantially fills the intake 42 so that all air drawn through the air intake 42 must pass through the filter 60. The filter 60 is preferably not a high-density filter, but is instead designed to intercept and retain only fairly large particulates such as dust. The purpose of the filter 60 is not to allow the apparatus 10 to cleanse particulates from the air, but is merely to intercept dust over 10 microns in size that would otherwise contaminate the ultraviolet light bulbs described below. In a preferred embodiment, the filter is model no. AG300, available from Airguard Industries located in Louisville, Kentucky. The filter 60 is retained in the air intake 42 by means of clips, brackets or any other suitable retention means (not shown) that allow easy removal and replacement of the filter 60.

The air discharge 44 is preferably positioned remotely from the air intake 42, so that the exhausted air circulates into the environment rather than being immediately drawn back into the apparatus 10. In the embodiment shown in FIG. 1, the air discharge is on the upper portion of the front 46 of the housing 40 while the air intake 42 is positioned toward the rear wall 14 on the lower wall 12 of the housing 40. This produces a circulatory effect through the environment of the apparatus 10 by drawing air into the apparatus 10 through the air intake 42 and expelling air from the apparatus 10 through the air discharge 44, roughly in the direction of the arrows shown in FIG. 2. The air discharge 44 is preferably covered with a grill 48 to prevent the introduction of hands or objects into the air discharge 44 and to diffuse the air stream. It is notable that in the preferred embodiment, the air discharge 44 does not include any filter to remove particulates, but only includes this protective grill 48. Therefore, the only filter in the preferred embodiment is the large particulate filter 60 positioned in the air intake 42. The apparatus 10 is designed to allow small particulates, including microdroplets of sputum containing bacteria that are destroyed by the ultraviolet lights as described below, to be expelled back into the environment. As a result, the apparatus does not have a site that traps and allows the colonization of bacteria, which would require frequent cleaning or sterilization. In addition, there is very little resistance to air flow, thereby allowing the use of a relatively small, low-energy and quiet motor and blower system, as further described below.

In this respect, the present system is fundamentally different from prior art devices that are designed to remove dirt, pollen and other particulates and odor from the air. Those prior art systems employ dense and multiple filters and noisy high-energy blowers to indiscriminately remove impurities from the air. But they are not specifically for the purpose of destroying pathogenic pulmonary bacteria such as tuberculosis and their efficiency in doing so is undocumented and questionable. In contrast, the present system is specifically designed for destroying bacteria such as the tuberculosis bacteria, and is highly effective in accomplishing that using a relatively small, energy efficient, quiet apparatus, but the present system makes no attempt at all to remove impurities from the air. Even the bacteria itself is released back to the environment once it is killed by the apparatus.

Figures 2, 3:
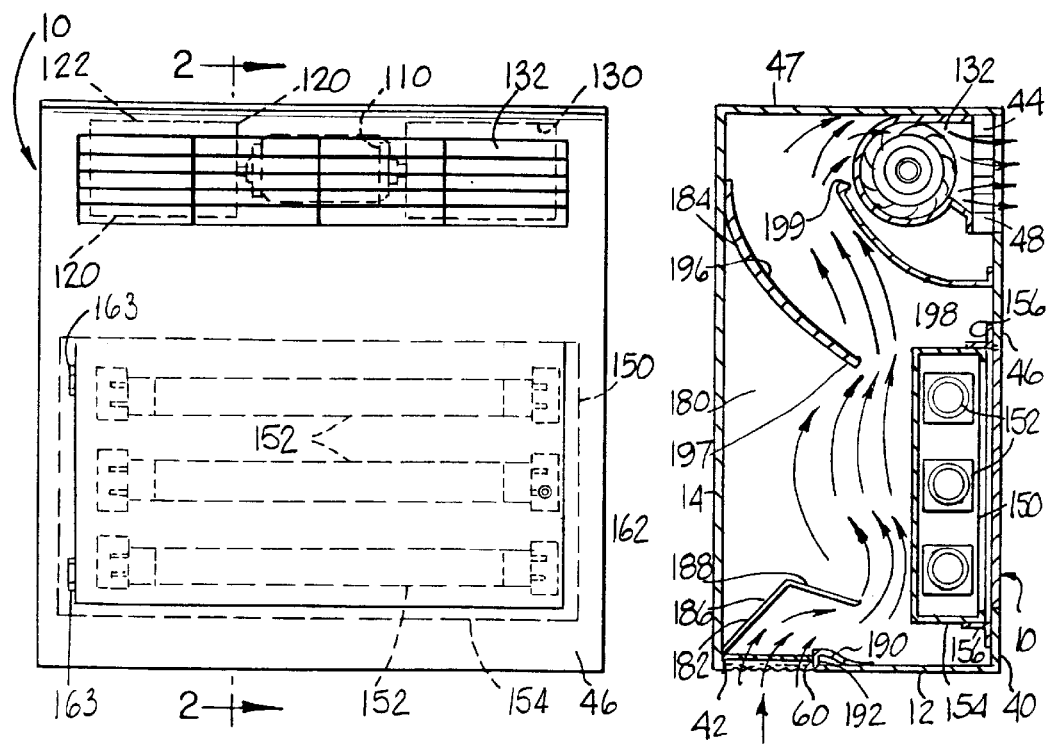
FIG. 2 is a side sectional view of the present invention, taken along ine 2—2 of FIG. 3.
FIG. 3 is a front elevational view of the present invention.
Figure 4:
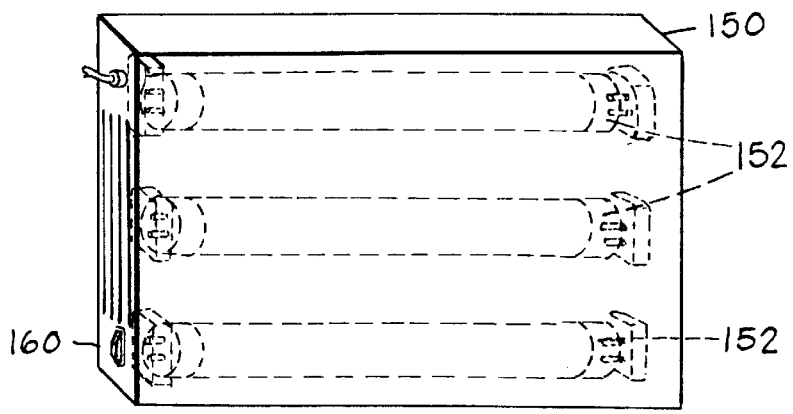
FIG. 4 is a pictorial view of the casing for the ultraviolet light bulbs of the present invention.

Positioned in the interior of the housing 40 is an ultraviolet light box 150, which is shown in the side sectional view of FIG. 2, the front view of FIG. 3 and the pictorial detail of FIG. 4. The light box 150 directs ultraviolet light into a sterilization chamber 180 in the interior of the housing, where air flows from the air intake 42 to the air discharge 44. It includes at least one ultraviolet light 152 (three in the embodiment shown in the figures) enclosed by a casing 154 which is mounted to the interior of the housing 40 by an appropriate mount such as the ultraviolet light box mounting brackets 156 shown in FIG. 2. The exact structure of the casing 152 is not critical, provided that is includes electrical sockets to receive the ultraviolet lights 152 with sufficient support to retain them, a means to mount the casing 150 to the housing 40, and a light-emitting side 160 that allows light to be transmitted from the ultraviolet lights 152 to the sterilization chamber 180. The light-emitting side 160 may simply be open so that there is nothing between the ultraviolet light bulbs 152 and the sterilization chamber 180, or there may be a transparent dust cover over the light box so that light is transmitted from the ultraviolet lights bulbs 152, through the transparent cover and into the sterilization chamber 180. The ultraviolet lights 152 are accessed for cleaning and replacing through an access door 162 in the front wall 46 of the housing 40. The access door 162 may be mounted to the front wall 46 of the housing 40 by a set of hinges 163 or other suitable mounting means.

The sterilization chamber 180 is baffled adjacent the air intake 42 by an intake baffle 182 and adjacent the air discharge 44 by an exhaust baffle 184, to prevent ultraviolet light from leaking from the sterilization chamber 180 out the air intake 42 or air discharge 44 and into the environment where it could damage the skin and eyes of patients and other persons. The intake baffle 182 in the preferred embodiment includes a rear inclined portion 186 extending upward and forward between the air intake 42 and the back wall 14 of the housing 40. The rear inclined portion 186 joins an upper inclined portion 188 which extends downward and forward. A forward vertical portion 192 extends upward from the front edge of the air intake 42 and joins a forward inclined portion 190 which extends downward and forward. A forward vertical portion 192 extends upward from the front edge of the air intake 42 and joins a forward inclined portion 190 which extends downward and forward. The forward inclined portion 190 and upper inclined portion 188 at their forward edges form an intake baffle opening 194 through which the interior of the intake baffle 182 is in communication with the sterilization chamber 180.

The exhaust baffle 184 includes an inclined rear portion 196, the top of which is attached to the interior of the rear wall 14 of the housing 40, and which slopes forward and downward. The exhaust baffle 184 also includes an inclined forward portion 198, the bottom of which is attached to the interior of the front wall 46 of the housing 40. The forward edge 197 of the inclined rear portion 196 and the bottom side of the inclined forward portion 198 form an opening between the sterilization chamber 180 and the blowers described below. The opening extends upward into the channel between the inclined rear portion 196 and the inclined forward portion 198. The top edge 199 of the inclined forward portion 198 and the top wall 47 of the housing 40 form another opening. Therefore, a channel is constituted by the opening between the bottom edge 197 of the inclined rear portion 196 and the inclined forward portion 198, which extends upward through a channel formed between the inclined rear portion 196 and the inclined forward portion 198, through the opening between the upper edge 199 of the inclined forward portion 198 and the interior of the upper wall 47 of the housing 40, and then into the blowers described below.

Thus it can be appreciated that for any ultraviolet light to escape through the air discharge 44, it must reflect off the walls of the sterilization chamber 180, up through the exhaust baffle 184 by multiple reflections off the inclined rear portion 184 and inclined forward portion 198, and then through the blowers and out the air exhaust grill 48. For any ultraviolet light to escape through the air intake 42, it must reflect off the walls of the sterilization chamber 180, and down through the intake baffle 182 by multiple reflections of the rear inclined portion 186, upper inclined portion 188, vertical portion 192 and forward inclined portioned 190, and then out through the air intake filter 42. The possibility of light escaping can be further reduced by applying an absorptive coating or paint to the interior surfaces of the baffles 182 and 184.

Although the baffling described above to prevent ultraviolet light from escaping presents a circuitous route for the passage of air from the air intake 42 through the sterilization chamber 180 and out the air discharge 44, the baffles are still designed to minimize the resistance to air flow. Thus, as shown by the arrows in FIG. 2, the air can flow reasonably smoothly with limited turbulence loses, thereby allowing a small, quiet and efficient blower system.

The blower system in the preferred embodiment includes a pair of "squirrel-cage" type blowers 120 and 130 which are driven by a motor 110. The blowers 120 and 130 draw air through their ends and propel the air out exhaust ports 122 and 132, respectively which mate with the air discharge 44 of the housing 40. The exact size of the blowers and motor depend on the desired use of the machine and the size of the environment in which it will be used, as further discussed below. The motor is preferably of the normal alternating current type and is in communication with the electrical system of the apparatus, which also powers the ballasts for the ultraviolet lights 152. The electrical system is ordinary, and the details of it will be apparent to those skilled in the wiring of lights and motors, and is not further described herein.

Figure 5:
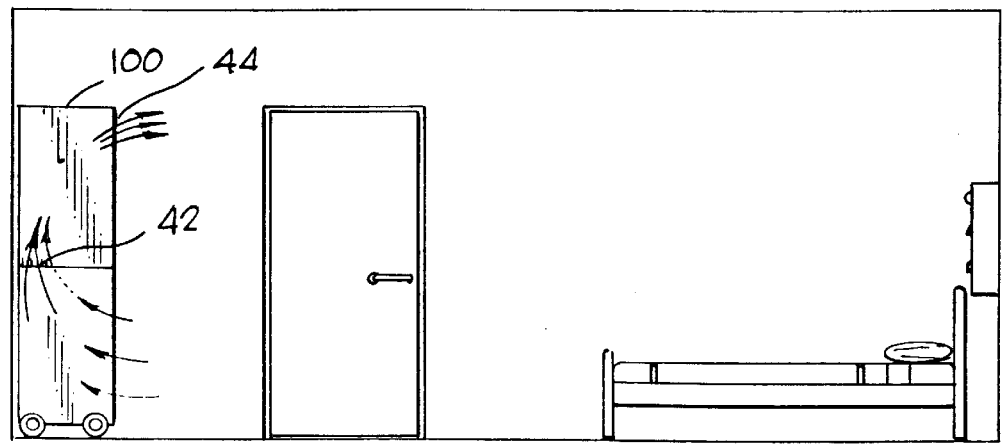
FIG. 5 is a side elevational view of the invention installed in a patient room.

The apparatus 10 is preferably positioned in a patient room so that the air intake 42 is approximately at the height of the head of a seated patient in order to intercept microdroplets that are released by the patient into the room, such as shown in a preferred arrangement in FIG. 5. The microdroplets from the patient are expectorated from the patient into the surrounding air where they are suspended. The air currents produced by the apparatus 10 draws air into the apparatus 10 from roughly the height of the air intake 42. The air with the suspended microdroplets passes through the sterilization chamber where the bacteria are destroyed, and the air along with the suspended microdroplets with the then-killed bacteria are expelled from the apparatus 10 back into the room through the air discharge 44. Because the air discharge 44 is preferably positioned at the top of the apparatus 10 while the air intake 42 is positioned at the bottom of the apparatus, the air being drawn into the air intake 42 and expelled from the air discharge 44 produces a circulatory effect through the room which increases the flow of new unsterilized air into the apparatus. This circulatory effect also helps prevent the air from short-circuiting the circulation pattern by leaving the apparatus 10 through the air discharge 44 and immediately re-entering the apparatus 10 through the air intake 42 without passing through the room.

It has been determined experimentally that transmission of the tuberculosis bacteria from an infected patient to an uninfected person can be effectively prevented by ensuring that there is approximately 10 to 15 air changes per hour in the patient room using the apparatus and positioning described above. The phrase "10 to 15 air changes per hour" means a circulatory effect through the apparatus in which the total volume of air through the apparatus per hour equals the air volume of the room multiplied times a number between 10 and 15, inclusive. For example, one air change per hour in a 1,000 cubic foot room would require an apparatus through which 1,000 cubic feet of air pass per hour. Therefore, in a patient room having dimensions of 10 by 10 by 10 feet for a total volume of 1,000 cubic feet, or other dimensions for a total volume of 1,000 cubic feet, the apparatus should be capable of circulating through it at the rate of 10,000 to 15,000 cubic feet of air per hour.

The exact dimensions of the apparatus to achieve such a flow rate in a preferred embodiment include a housing 40 having a length and height of about 36 inches and a depth of about 18 inches. The air intake 42 is roughly 36 inches by 8 inches and the air discharge is roughly 32 inches by 8 inches. The opening between the upper inclined portion 188 and the forward inclined portion 190 of the intake baffle 182 about four inches, and the opening between the inclined rear portion 196 and the inclined forward portion 198 of the exhaust baffle 184 is about six inches. The motor 110 is a 115 volt, 1150 rpm motor, and the pair of blowers 120 and 130 include 7 by 4 inch blower wheels. The ultraviolet lights 152 are model D-36-3 by American U.V. Co.

It can be appreciated that the preferred embodiment described above is small and light-weight enough that it can be transported from room to room depending on patient needs. Therefore, the apparatus 10 may be designed to be bolted to a wall of the room. Alternatively or in addition, it may be designed to be placed on a movable surface such as the wheeled cart 170 shown in FIG. 5. In that way, the apparatus is easily moved from room to room or moved within a given room as patient and hospital needs may dictate. By utilizing a cart 170 such as the one shown in FIG. 5, rather than simply mounting the apparatus 10 on casters, the apparatus is maintained at the height of the patient to ensure effective interception of bacteria.

Figure 6:
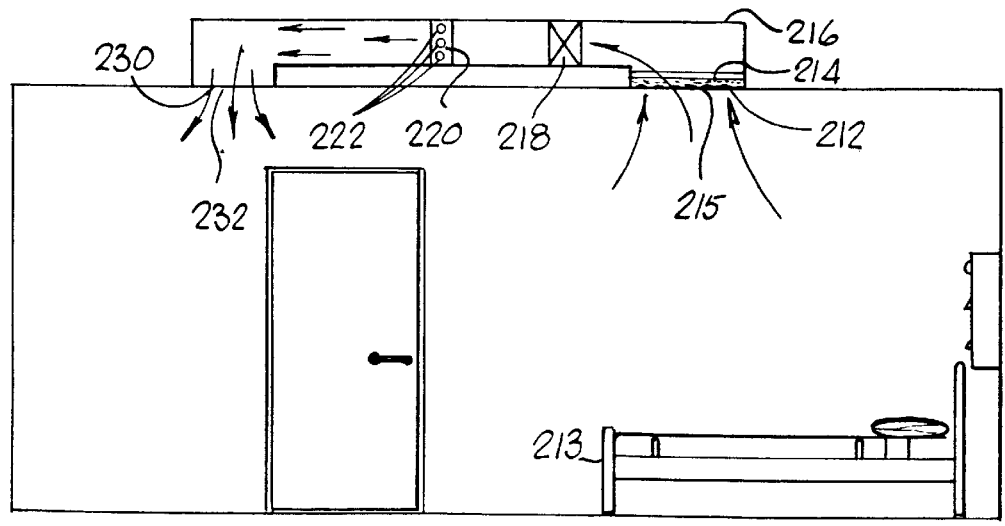
FIG. 6 is a side sectional view of an alternative embodiment of the invention in a patient room.

An alternative embodiment of the invention is shown in FIG. 6, in which the system is installed in the ceiling of a room. An air intake 212 is positioned in the ceiling above a patient area such as a bed 213. The relative positioning of the patient bed, the door, and the intake and discharge for the appratus may be other than as shown. The air intake 212 may have an intake filter 214 such as model AG300 from Airguard Industries of Louisville, Ky. The filter 214 may be covered by a grill 215. An air duct 216 opens to the air intake 212 and encloses a blower 218. An ultraviolet light box 220 houses one or more ultraviolet light bulbs 222. The light box 220 is configured such that air can pass through it and between the several ultraviolet light bulbs 222 in the direction of the air duct 216. An air exhaust 230 is positioned in the air duct 216 at the opposite and from the air intake 212. As in the case of the air intake 212, the air exhaust 230 may be covered with a grill 232.

In operation, the blower 218 draws air from the vicinity of the air intake 212 near the patient, and up into the air duct 216. As the air passes through the filter 214, large particulates such as dust are trapped by the filter so that they do not contaminate the ultraviolet light bulbs 222. The filter is a low density filter, so that smaller particulates including microdroplets of sputum which may contain viable bacteria are not trapped by the filter 214 but instead continue up through the air duct 216. The air with suspended microdroplets is drawn through the blower 218 and is propelled further through the air duct 216 so that it passes through the ultraviolet light box 220. The ultraviolet light bulbs 222 sterilize the air, and the air with the killed bacteria and other small particulates continues to be propelled down the air duct 216 and out the air exhaust 230 and back into the room.

What is claimed is:

1. A method for destroying airborne tuberculosis bacteria in the air in a room, comprising drawing air into a device, filtering the air using a filter mounted on the device, drawing the air through a sterilization chamber in the device having at least one ultraviolet light bulb for irradiating the air with germicidal ultraviolet light at an air flow rate that is calculated to produce at least ten air exchanges per hour in the room, and releasing the air including destroyed bacteria back into the room, wherein the device includes an air intake opening for air to enter the device and wherein the filter is positioned between the air intake opening and the sterilization chamber whereby substantially all air that enters the sterilization chamber passes first through the filter and wherein the sterilization chamber includes an air intake baffle to prevent ultraviolet light from escaping from the sterilization chamber through the air intake opening and into the room.

2. The method of claim 1, wherein the filter traps substantially no particulates and droplets smaller than 10 microns in diameter.

3. The method of claim 1, wherein the air intake baffle includes an intake channel enclosed by intake channel walls and surrounding the air intake opening and extending into the sterilization chamber, the intake channel being configured such that light cannot pass from the sterilization chamber through the intake channel and out the air intake opening except by reflecting off at least one intake channel wall.

4. The method of claim 3, wherein the intake channel is configured such that light cannot pass from the sterilization chamber through the intake channel and out the air intake opening except by reflecting off a plurality of intake channel walls.

5. The method of claim 4, wherein the releasing of the air including the destroyed bacteria back into the room is through an air exhaust opening in the device, and wherein the sterilization chamber includes an air exhaust baffle to prevent ultraviolet light from escaping from the sterilization chamber through the air exhaust opening and into the room.

6. The method of claim 5, wherein the air exhaust baffle includes an exhaust channel enclosed by exhaust channel walls and surrounding the air exhaust opening and extending into the sterilization chamber, the air exhaust channel being configured such that light cannot pass from the sterilization chamber through the exhaust channel and out the exhaust opening except by reflecting off at least one exhaust channel wall.

7. The method of claim 6, wherein the exhaust channel is configured such that light cannot pass from the sterilization chamber through the exhaust channel and out the air exhaust opening except by reflecting off a plurality of exhaust channel walls.

8. The method of claim 7, wherein at least one of the intake channel and exhaust channel is coated with an ultraviolet light-absorptive coating to absorb ultraviolet light incident thereon.

* * * * *